(12) United States Patent
Wiederin

(10) Patent No.: US 10,247,432 B1
(45) Date of Patent: Apr. 2, 2019

(54) SYSTEM FOR HUMIDIFYING GAS STREAMS

(71) Applicant: Elemental Scientific, Inc., Omaha, NE (US)

(72) Inventor: Daniel R. Wiederin, Omaha, NE (US)

(73) Assignee: Elemental Scientific, Inc., Omaha, NE (US)

( * ) Notice: Subject to any disclaimer, the term of this patent is extended or adjusted under 35 U.S.C. 154(b) by 377 days.

(21) Appl. No.: 15/018,576

(22) Filed: Feb. 8, 2016

Related U.S. Application Data

(60) Provisional application No. 62/112,693, filed on Feb. 6, 2015.

(51) Int. Cl.
| | |
|---|---|
| *F24F 6/04* | (2006.01) |
| *B01F 3/04* | (2006.01) |
| *F24F 6/12* | (2006.01) |
| *F24F 6/00* | (2006.01) |

(52) U.S. Cl.
CPC .............. *F24F 6/04* (2013.01); *B01F 3/0446* (2013.01); *B01F 3/04439* (2013.01); *F24F 6/12* (2013.01); *F24F 2006/008* (2013.01)

(58) Field of Classification Search
CPC ................ B01F 3/04439; B01F 3/0446; B01F 3/04007; F24F 6/04; F24F 6/10; F24F 6/12; F24F 2006/008
USPC .............................. 261/75, 104, 119.1, 142
See application file for complete search history.

(56) References Cited

U.S. PATENT DOCUMENTS

| 4,155,961 | A * | 5/1979 | Benthin | A61M 16/16 128/204.13 |
|---|---|---|---|---|
| 4,355,636 | A * | 10/1982 | Oetjen | A61M 16/16 128/204.13 |
| 4,367,734 | A * | 1/1983 | Benthin | A61M 16/16 128/204.13 |
| 4,381,267 | A * | 4/1983 | Jackson | A61M 16/16 128/204.13 |
| 5,738,808 | A * | 4/1998 | Iwamoto | A61M 16/16 128/204.13 |
| 6,896,247 | B2 * | 5/2005 | Brotzeller | G01N 23/20 261/104 |
| 7,866,637 | B2 * | 1/2011 | Van Der Net | C10J 1/06 261/104 |
| 7,975,992 | B2 * | 7/2011 | Bitoh | H01M 8/04126 261/104 |
| 2004/0245658 | A1 * | 12/2004 | Niland | A61M 16/16 261/104 |
| 2007/0246847 | A1 * | 10/2007 | Bitoh | H01M 8/04126 261/104 |

(Continued)

*Primary Examiner* — Charles S Bushey
(74) *Attorney, Agent, or Firm* — Kevin E. West; Advent, LLP

(57) ABSTRACT

In accordance with embodiments of this disclosure, a gas humidifier system includes a reservoir of liquid with at least one selectively permeable tube at least partially submerged within the liquid. A gas stream may be fed into the selectively permeable tube that passes through the liquid reservoir. The selectively permeable tube may be substantially impermeable to the gas flowing therethrough but permeable to vapor (e.g., water vapor) entering the selectively permeable tube from the liquid. Thus, vapor from the liquid reservoir can enter the selectively permeable tube and humidify the gas flowing therethrough.

10 Claims, 3 Drawing Sheets

(56) References Cited

U.S. PATENT DOCUMENTS

2013/0087936 A1\* 4/2013 Brenner ............... B01D 69/02
                                                    261/100

\* cited by examiner

SYSTEM FOR HUMIDIFYING GAS STREAMS

CROSS-REFERENCE TO RELATED APPLICATIONS

The present application claims priority under 35 U.S.C. § 119(e) to U.S. Provisional Application Ser. No. 62/112,693, filed Feb. 6, 2015 and titled "SYSTEM FOR HUMIDIFYING GAS STREAMS." U.S. Provisional Application Ser. No. 62/112,693 is incorporated herein by reference in its entirety.

BACKGROUND

For various applications including, but not limited to, inductively coupled plasma (ICP) emission or mass spectrometry, it is beneficial to humidify gas streams. Bubbling-type humidifiers with a single reservoir can be used to humidify a flow of dry gas, which can be divided into two or more streams after humidification. To accurately control flow rate, the wet (humidified) gas must pass through a control device (e.g., gas flow controller). A drawback to this approach is that the wet gas can cause corrosion or instability of the control device due to condensation. Additionally, a bubbling-type humidifier with a single reservoir is not able to simultaneously humidify two different gas streams having different chemical composition.

SUMMARY

The present disclosure is directed to a gas humidifier system that includes a reservoir of liquid with at least one selectively permeable tube at least partially submerged within the liquid. At either ambient or elevated temperature, the liquid is used to humidify one or more independently controlled gas streams. In some embodiments, each gas stream is fed into a respective selectively permeable tube that passes through the liquid reservoir. A flow rate of each gas stream can be controlled, independently, before the dry (non-humidified) gas is directed through the liquid reservoir (i.e., through a submerged portion of the respective selectively permeable tube). The selectively permeable tube may be substantially impermeable to the gas flowing therethrough but permeable to vapor (e.g., water vapor) entering the selectively permeable tube from the liquid. Thus, vapor from the liquid reservoir can enter the selectively permeable tube and humidify the gas flowing therethrough.

This Summary is provided to introduce a selection of concepts in a simplified form that are further described below in the Detailed Description. This Summary is not intended to identify key features or essential features of the claimed subject matter, nor is it intended to be used as an aid in determining the scope of the claimed subject matter.

DRAWINGS

The Detailed Description is described with reference to the accompanying figures. The use of the same reference numbers in different instances in the description and the figures may indicate similar or identical items.

DETAILED DESCRIPTION

Overview

Inductively coupled plasma (ICP) emission or mass spectrometry techniques can be used to measure the presence of chemical elements in liquid samples. In most cases, before introduction to the ICP, liquid samples are first dispersed into an aerosol by introduction of a first gas called nebulizing gas (e.g., argon) into a nebulizer. The nebulized aerosol can then be directed into a spray chamber which has physical properties that impact and remove the larger aerosol particles and direct the desirable fine aerosol particles into an ICP injector and then into the ICP for atomization and ionization followed by measurement using the spectrometer.

In some cases a second gas is introduced through a second port of the spray chamber to independently optimize instrument signal or to provide a convenient mechanism for controlling the rate of introduction of nebulized aerosol into the ICP, thereby controlling the extent of matrix suppression when samples with high levels of dissolved solids (>0.1% by weight) are analyzed.

The first gas and second gas flows or streams may be accurately controlled, both in total and relative to each other, to ensure instrument stability. A third or fourth spray chamber gas stream can also be used. For example, the addition of gases such as $O_2$ or $CH_4$ can be used for applications including, but not limited to, the analysis of organic solvents or for detection of low levels of elements such as As and Se.

Common sources of the first and second gases include compressed gas cylinders or liquefied gas, which at atmospheric pressure produce a gas with low humidity. When liquid samples include solutions containing a high concentration of dissolved solids (e.g., greater than 0.1% by weight) it is beneficial to humidify the first gas (nebulizer gas) to prevent formation of salt deposits in the nebulizer which would otherwise lead to instrument drift. Humidification of the second gas stream can also be beneficial to wet the aerosol particles and provide a wet surface to which the larger aerosol particles can adhere, helping to ensure that the larger aerosol particles are sorted from the desired fine aerosol.

Example System Implementations

Figure 1:
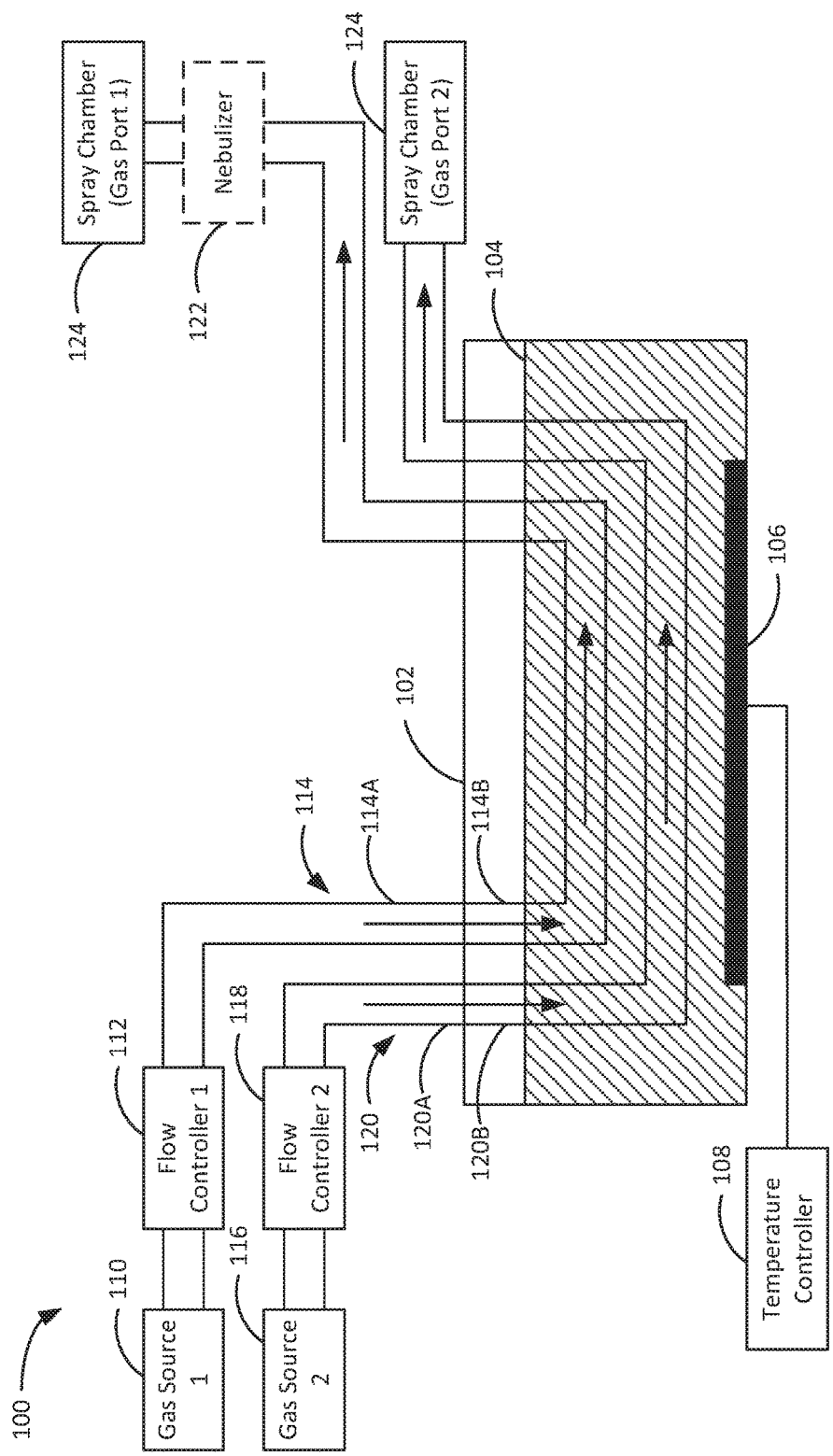
FIG. 1 is schematic diagram of a gas humidifying system in accordance with embodiments of this disclosure.
Figure 2A:
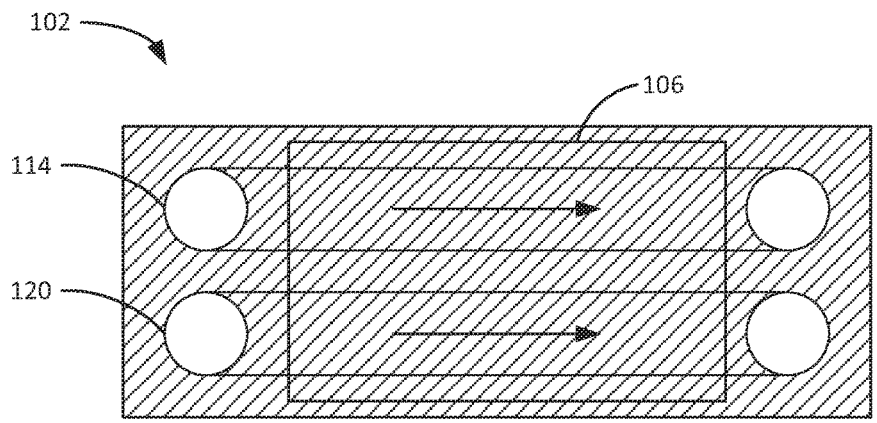
FIG. 2A is a top view of a liquid reservoir of the gas humidifying system in accordance with embodiments of this disclosure.
Figure 2B:
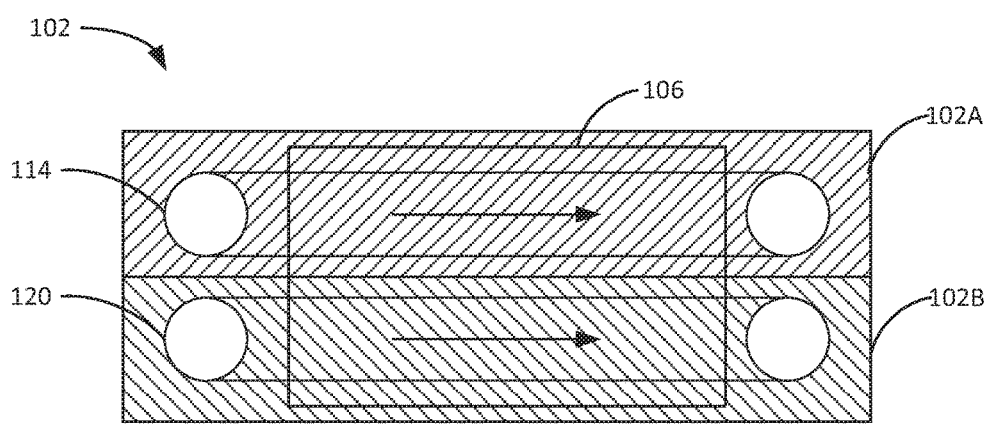
FIG. 2B is a top view of multiple adjacent liquid reservoirs of the gas humidifying system in accordance with embodiments of this disclosure.

FIGS. 1 through 2B illustrate a gas humidifying system 100 in accordance with various embodiments of this disclosure. Those skilled in the art will appreciate that the embodiments illustrated in the drawings and/or described herein may be fully or partially combined and/or modified to result in additional embodiments. Accordingly, the illustrated and described embodiments should be understood as explanatory and not as limitations of the present disclosure.

In an embodiment illustrated in FIG. 1, the gas humidifying system 100 is shown to include a reservoir 102 containing a liquid 104 (e.g., water). The system further includes at least one selectively permeable tube 114 (e.g., NAFION tubing) fluidically coupled with a gas source 110, where the selectively permeable tube 114 is at least partially submerged within the liquid 104. In some embodiments, the selectively permeable tube includes a first portion 114A, which may or may not be selectively permeable, and a second portion 114B that is selectively permeable. For example, the selectively permeable portion 114B or the entire tube 114 can be substantially impermeable to gas flowing therethrough from the gas source 110 and at least partially permeable to vapor entering the selectively permeable tube 114 from the liquid 104. Thus, vapor from the liquid 104 in the reservoir 102 can enter the selectively permeable tube 114 and humidify the gas stream flowing therethrough.

In some embodiments, the first portion 114A and the second portion 114B are separate tubes, where at least the second tube 114B is selectively permeable. For example, the first tube 114A may be connected to an exterior port of the reservoir 102, and the second (selectively permeable) tube may be connected to an interior port of the reservoir 102, where the exterior port and the interior port are fluidically coupled to one another.

In some embodiments, a gas flow controller 112 (e.g., a manually or electromechanically controllable valve) is fluidically coupled with the gas source 112 and the selectively permeable tube 114. The gas flow controller 112 can be configured to control a flow rate of a gas stream flowing from the gas source 110 prior to passage of the gas stream through a submerged portion of the selectively permeable tube 114. By controlling the gas flow rate of the gas stream prior to humidification, corrosion or instability of the gas flow controller 112 may be prevented.

For ICP spectrometry applications, among others, a nebulizer 122 (e.g., an analytical nebulizer) can be fluidically coupled with the selectively permeable tube 114. The nebulizer 112 may be configured to receive and nebulize a (humidified) gas stream flowing from the gas source 110 after passage of the gas stream through a submerged portion of the selectively permeable tube 114. The nebulized gas can then be fed from the nebulizer 122 into a spray chamber 124 via a respective port (e.g., Gas Port 1).

In some embodiments, the system 100 further includes a heating element 106 thermally coupled with or forming a portion of the reservoir 102. The heating element 106 can serve to heat the liquid to a controlled temperature. For example, the heating element can be manually controlled (e.g., with an adjustable knob or valve) or electronically controlled via a temperature controller 108 including electronic control circuitry.

As shown in FIG. 1, the system 100 can be configured to simultaneously humidify multiple gas streams from independent sources. For example, the system can include at least a second selectively permeable tube 120 fluidically coupled with a second gas source 116, where the second selectively permeable tube 120 is at least partially submerged within the liquid 104. In some cases, the second gas source 116 contains a different chemical composition (i.e. provides a different gaseous substance) than the first gas source 110. Because the tubes 114 and 120 are selectively permeable, the different gaseous substances provided by the first gas source 110 and the second gas source 116 can be directed through the same reservoir 102 (an humidified by the liquid 104 contained therein) without any risk of cross-contamination. As described above with regard to the first selectively permeable tube 114, the second selectively permeable tube 120 can include separate portions/tubes 120A and 120B, where at least the inner portion/tube 120B is selectively permeable. The second selectively permeable tube 120 can also be fluidically coupled with the spray chamber 124 via a respective port (e.g., Gas Port 2) for ICP spectrometry, as discussed above, or for other applications requiring two or more simultaneous humidified gas streams.

FIG. 2A shows a top view of the reservoir 102 with the first selectively permeable tube 114 and the second selectively permeable tube 120 at least partially submerged within the liquid 104 contained therein. FIG. 2B shows another embodiment of the system 100, where the reservoir 102 is partitioned into a first reservoir 102A and a second reservoir 102B adjacent to the first reservoir 102A. Each of the reservoirs/partitions 102A and 102B can have a respective one of the first and second selectively permeable tube 114 and 120 at least partially submerged within the liquid contained therein. This can be beneficial for some applications, for example, where sensitivity to cross-contamination is very high or where a different liquid used for humidifying each gas stream. The embodiment shown in FIG. 2B is illustrative of one implementation; however, it is to be understood that each of the first and second reservoirs 102A and 102B can be independent (i.e., not formed from partitions of reservoir 102).

In some embodiments, the liquid within the first and second reservoirs 102A and 102B is thermally controlled by the same heating element 106. For example, the heating element 106 can be thermally coupled with or can form a portion of each of the first reservoir 102A and the second reservoir 102B.

Those skilled in the art will appreciate the foregoing embodiments are not exhaustive. For example, the system 100 can include any number of reservoirs 102 having one or more selectively permeable tubes (e.g., tubes 114 and 120) at least partially submerged within the liquid 104 contained therein.

Example Process Implementations

Figure 3:
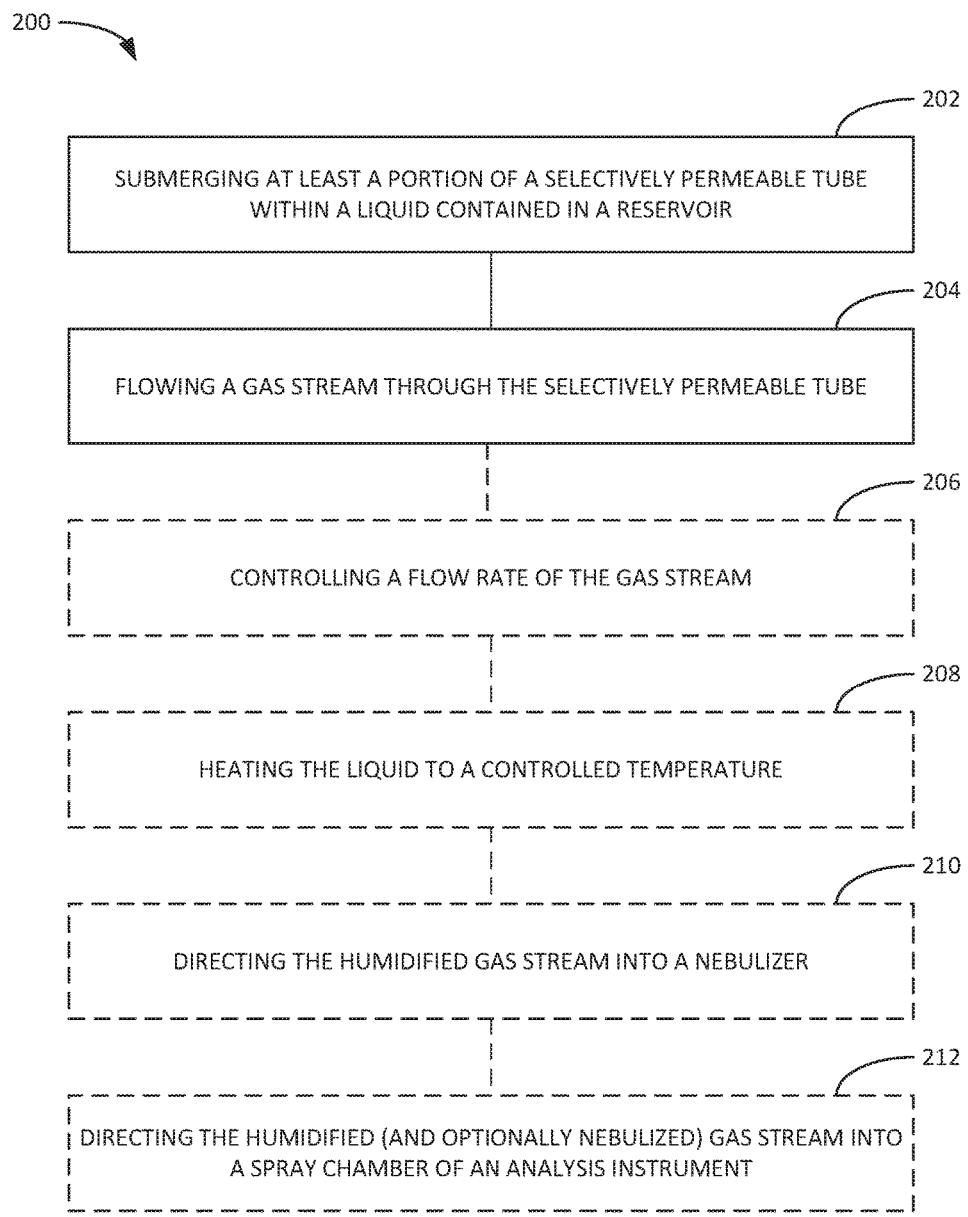
FIG. 3 is a flow diagram illustrating a method of humidifying at least one gas stream in accordance with implementations of this disclosure.

FIG. 3 is a flow diagram illustrating a method 200 for humidifying at least one gas stream in accordance with one or more disclosed implementations. In some implementations, the method 200 can be executed utilizing the system 100 described herein. In this regard, in addition to the steps or operations described below, the method 200 can further include any steps or operations disclosed with regard to embodiments of the system 100 described herein.

At block 202, a selectively permeable tube (e.g., a tube such as tube 114) is submerged within a liquid contained in a reservoir (e.g., water or any other appropriate liquid contained in a reservoir such as reservoir 102). In some implementations, only a portion of the partially submerged tube is selectively permeable (e.g., part or all of the submerged portion). In other implementations, the entirety of the tube is selectively permeable (i.e., permeable to vapor entering from the liquid in the reservoir but substantially impermeable to a gas stream flowing through the tube).

At block 204, a gas stream is flowed through the selectively permeable tube so that the gas stream can be humidified by vapor entering the tube from the liquid in the reservoir. For example, gas from a gas source, such as gas source 110, is directed into the selectively permeable tube, which is at least partially submerged in the liquid.

At block 206, the flow rate of the gas is optionally controlled (e.g., using a flow controller such as flow controller 112). In some implementations, the flow rate of the gas may be adjusted by a flow controller before the gas is flowed through the submerged portion of the selectively permeable tube.

At block 208, the temperature of the liquid in the reservoir is optionally controlled. For example, the liquid can be heated with a heating element, such as heating element 106 (e.g., a resistive, inductive, or electromagnetic (e.g., microwave) heating element). The heating element may be manually controlled (e.g., with an adjustable knob or valve) or electronically controlled via a temperature controller (e.g., temperature controller 108) that includes electronic control circuitry and/or a processor, microcontroller, ASIC, programmable logic device, or the like.

At blocks 210 and 212, the humidified gas stream (i.e., having passed through the submerged portion of the selectively permeable tube) may be supplied for analysis (e.g., for ICP emission or mass spectrometry analysis). At block 210, the humidified gas stream is optionally directed into a nebulizer, such as nebulizer 122. At block 212, the humidified gas stream in introduced into a spray chamber (e.g., spray chamber 124) of an analysis instrument (e.g., an ICP emission or mass spectrometry analysis instrument or the like). The spray chamber may be coupled to the instrument or can form a portion thereof, and is configured to direct at least a portion of the humidified (and optionally nebulized) gas to an analysis site (e.g., ICP torch) of the analysis instrument.

Furthermore, it is to be understood that the invention is defined by the appended claims. Although embodiments of this invention have been illustrated, it is apparent that various modifications may be made by those skilled in the art without departing from the scope and spirit of the disclosure.

What is claimed is:

1. A system, comprising:
   a first gas source;
   a first reservoir of liquid;
   a first selectively permeable tube fluidically coupled with the first gas source, the first selectively permeable tube being at least partially submerged within the first reservoir of liquid;
   a first gas flow controller fluidically coupled with the first gas source and the first selectively permeable tube, the first gas flow controller being configured to control a flow rate of a first gas stream from the first gas source prior to passage of the first gas stream through a submerged portion of the first selectively permeable tube;
   a first nebulizer fluidically coupled with the first selectively permeable tube, the first nebulizer being configured to receive and nebulize the first gas stream from the first gas source after the first gas stream flows through a submerged portion of the first selectively permeable tube;
   a first heating element thermally coupled with or forming a portion of the first reservoir, the first heating element being configured to heat the first reservoir of liquid to a first controlled temperature; and
   a first temperature controller configured to control a temperature of the first reservoir of liquid to the first controlled temperature;
   a second gas source, the second gas source comprising a gas with a different chemical composition than the first gas source;
   a second reservoir of liquid;
   a second selectively permeable tube fluidically coupled with the second gas source, the second selectively permeable tube being at least partially submerged within the second reservoir of liquid;
   a second heating element thermally coupled with or forming a portion of the second reservoir, the second heating element being configured to heat the second reservoir of liquid to a second controlled temperature; and
   a second temperature controller configured to control a temperature of the second reservoir of liquid to the second controlled temperature.

2. The system of claim 1, further comprising: a second nebulizer fluidically coupled with the second selectively permeable tube, the second nebulizer being configured to receive and nebulize a second gas stream after the second gas stream flows through a submerged portion of the second selectively permeable tube.

3. The system of claim 1, wherein the first selectively permeable tube is substantially impermeable to gas flowing therethrough from the first gas source and is at least partially permeable to vapor entering the first selectively permeable tube from the liquid of the first reservoir, and wherein the second selectively permeable tube is substantially impermeable to gas flowing therethrough from the second gas source and is at least partially permeable to vapor entering the second selectively permeable tube from the liquid of the second reservoir.

4. A system for humidifying at least two gas streams, comprising:
   a first gas source;
   a first reservoir of liquid;
   a first selectively permeable tube fluidically coupled with the first gas source, the first selectively permeable tube being at least partially submerged within the liquid of the first reservoir;
   a second gas source, the second gas source comprising a gas with a different chemical composition than the first gas source;
   a second reservoir of liquid;
   a second selectively permeable tube fluidically coupled with the second gas source, the second selectively permeable tube being at least partially submerged within the liquid of the second reservoir;
   a first gas flow controller fluidically coupled with the first gas source and the first selectively permeable tube, the first gas flow controller being configured to control a flow rate of a first gas stream from the first gas source prior to passage of the first gas stream through a submerged portion of the first selectively permeable tube;
   a second gas flow controller fluidically coupled with the second gas source and the second selectively permeable tube, the second gas flow controller being configured to control a flow rate of a second gas stream from the second gas source prior to passage of the second gas stream through a submerged portion of the second selectively permeable tube;
   a first nebulizer fluidically coupled with the first selectively permeable tube, the first nebulizer being configured to receive and nebulize a gas stream from the first gas source after passage of the gas stream through a submerged portion of the first selectively permeable tube;
   a first heating element thermally coupled with or forming a portion of the first reservoir, the first heating element being configured to heat the liquid of the first reservoir to a first controlled temperature;
   a second heating element thermally coupled with or forming a portion of the second reservoir, the second heating element being configured to heat the liquid of the second reservoir to a second controlled temperature;
   a first temperature controller configured to control a temperature of the liquid of the first reservoir to the first controlled temperature; and a second temperature controller configured to control the temperature of the liquid of the second reservoir to the second controlled temperature.

5. The system of claim 4, wherein the first reservoir is adjacent to the second reservoir.

6. The system of claim 4, further comprising: a second nebulizer fluidically coupled with the second selectively permeable tube, the second nebulizer being configured to receive and nebulize a second gas stream after the second gas stream flows through a submerged portion of the second selectively permeable tube.

7. The system of claim 4, wherein the first selectively permeable tube is substantially impermeable to gas flowing therethrough from the first gas source and is at least partially permeable to vapor entering the first selectively permeable tube from the liquid of the first reservoir, and wherein the second selectively permeable tube is substantially impermeable to gas flowing therethrough from the second gas source and is at least partially permeable to vapor entering the second selectively permeable tube from the liquid of the second reservoir.

8. A method, comprising:
submerging at least a portion of a first selectively permeable tube within a liquid contained in a first reservoir;
flowing a first gas stream through the first selectively permeable tube;
controlling a flow rate of the first gas stream prior to flowing the first gas stream through the submerged portion of the first selectively permeable tube;
heating the liquid contained in the first reservoir to a first controlled temperature via a first heating element;
directing and nebulizing the first gas stream via a first nebulizer after flowing the first gas stream through the submerged portion of the first selectively permeable tube;
controlling a temperature of the liquid contained in the first reservoir to the first controlled temperature via a first temperature controller;
submerging at least a portion of a second selectively permeable tube within a liquid contained in a second reservoir;
flowing a second gas stream through the second selectively permeable tube;
controlling a flow rate of the second gas stream prior to flowing the second gas stream through the submerged portion of the second selectively permeable tube;
heating the liquid contained in the second reservoir to a second controlled temperature via a second heating element;

directing and nebulizing the second gas stream via a second nebulizer after flowing the second gas stream through the submerged portion of the second selectively permeable tube; and controlling a temperature of the liquid contained in the second reservoir to the second controlled temperature via a second temperature controller.

9. The method of claim 8, further comprising:

directing the first gas stream into a spray chamber of an analysis instrument after flowing the first gas stream through the submerged portion of the first selectively permeable tube and directing the second gas stream into a spray chamber of an analysis instrument after flowing the second gas stream through the submerged portion of the second selectively permeable tube.

10. The method of claim 8, wherein the first selectively permeable tube is substantially impermeable to gas flowing therethrough and is at least partially permeable to vapor entering the first selectively permeable tube from the liquid and the second selectively permeable tube is substantially impermeable to gas flowing therethrough and is at least partially permeable to vapor entering the second selectively permeable tube from the liquid.

* * * * *